(12) United States Patent
Fies

(10) Patent No.: US 6,346,156 B1
(45) Date of Patent: Feb. 12, 2002

(54) APPLICATION OF ALKYL POLYGLUCOSIDES IN PRINTING INK CLEANERS

(75) Inventor: Matthias Fies, Krefeld (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/530,695

(22) PCT Filed: Oct. 21, 1998

(86) PCT No.: PCT/EP98/06690

§ 371 Date: Jun. 23, 2000

§ 102(e) Date: Jun. 23, 2000

(87) PCT Pub. No.: WO99/22943

PCT Pub. Date: May 14, 1999

(30) Foreign Application Priority Data

Oct. 30, 1997 (DE) .......................................... 197 47 892

(51) Int. Cl.⁷ ................................................. B08B 3/04
(52) U.S. Cl. ............................ 134/42; 134/40; 510/170; 510/171; 510/172
(58) Field of Search ............................... 134/26, 32, 33, 134/38, 39, 40, 41, 42; 510/170, 171, 172, 174, 407

(56) References Cited

U.S. PATENT DOCUMENTS

| | | | |
|---|---|---|---|
| 4,664,721 A | * | 5/1987 | Valasek |
| 4,836,950 A | * | 6/1989 | Madsen et al. |
| 5,009,716 A | * | 4/1991 | Gerson |
| 5,616,548 A | | 4/1997 | Thomas et al. |

FOREIGN PATENT DOCUMENTS

| | | |
|---|---|---|
| EP | 0 498 545 A1 | 8/1992 |
| EP | 0 509 608 | 10/1992 |
| EP | 0 498 545 B1 | 10/1995 |

OTHER PUBLICATIONS

Database WPI, Section Ch, Week 9022, Derwent Publications Ltd., London, GB; Class E19, AN 90–167378, XP002092899 & JP 02 107492 A (Iwatsu Electric KK), Apr. 19, 1990.

* cited by examiner

Primary Examiner—Yogendra N. Gupta
Assistant Examiner—Gregory E. Webb
(74) Attorney, Agent, or Firm—John E. Drach; Steven J. Trzaska

(57) ABSTRACT

A process for removing printing inks and/or oil residues located on a surface of a printing apparatus comprising:

(a) contacting the printing inks and/or oil residues located on the surface of the printing apparatus with a cleaning composition containing an alkyl polyglycoside corresponding to formula (I):

$$R(G)_x \qquad (I)$$

wherein R is a linear saturated alkyl radical having from 8 to 22 carbon atoms, and $(G)_x$ is a glycoside or oligoglycoside radical having a degree of oligomerization, x, of from 1 to 10 to form a printing ink and/or oil residue emulsion; and (b) removing the printing inks and/or oil residue emulsion from the surface of the printing apparatus.

5 Claims, No Drawings

APPLICATION OF ALKYL POLYGLUCOSIDES IN PRINTING INK CLEANERS

BACKGROUND OF THE INVENTION

The invention relates to the use of alkyl polyglycosides in printing ink cleaners. The invention further relates to a method of removing printing inks and/or oil residues which form on the surface of printing machines, printing plates and the like and also the associated equipment, in which the surface is treated with a cleaning composition comprising at least one alkyl polyglycoside.

EP 498 545 B1 describes a method of removing oil residues which form on the surface of printing machines, printing plates and the associated equipment, said method comprising the following step: treating the surface with a cleaning composition which comprises at least one $C_6$ or higher alkyl ester of a fatty acid. In addition to these fatty acid esters, which function as the main constituent of the cleaning composition, other, complementary constituents may be present in the cleaning composition, examples being surfactants, emulsifiers, vegetable oils, fatty acid $C_{1-5}$ alkyl esters, water, organic solvents, acids, bases, alkalis, buffer systems, sequesterants, and corrosion inhibitors.

WO 94/17143 describes cleaning compositions for removing unwanted paint and similar "coatings" from a substrate, said compositions comprising 5-membered ring lactams and also triglycerides of monocarboxylic acids having 1 to 4 carbon atoms.

WO 90/03419 describes the use of $C_{1-5}$ alkyl esters of aliphatic $C_{8-22}$ monocarboxylic acids for removing fat, ink and the like from printing machines, specially offset printing machines. Said esters are used preferably in a blend with vegetable oils and a surfactant. Said surfactant is preferably selected from the class of the polyglycol ethers of aliphatic $C_{8-22}$ alcohols, very particular preference being given to adducts of from 7 to 14 mol of ethylene oxide per mole of a $C_{12-22}$ fatty alcohol.

DESCRIPTION OF THE INVENTION

It was an object of the present invention to provide new, effective printing ink cleaners. In particular, the intention was to provide a method of removing printing inks and/or oil residues which form on the surface of printing machines, printing plates and the like and also the associated equipment.

It has surprisingly been found that alkyl polyglycosides, which belong to the class of nonionic surfactants are suitable, alone or in combination with other substances, for sustained removal of printing inks from solid surfaces. In particular, said alkyl polyglycosides are suitable for removing printing inks and/or oil residues which form on the surface of printing machines, printing plates and the like and also the associated equipment.

In the context of the present invention the term "solid surface" is used in the sense that it embraces exclusively those applications where the surface to be cleaned is merely freed from unwanted deposits thereon, such as printing inks, printing ink residues, oil residues and the like but the surface per se is not destroyed in the course of this operation. Not part of the present invention, accordingly, are those applications where the removal of printing inks and the like is accompanied by substantial destruction or degradation of the surface, as is the case, for example, in the removal of printing inks from printed waste paper. In the case of this latter process, the paper used is not retained as such but instead, following the process, is in the form of fragments (paper fiber pulp).

The present invention provides for the use of alkyl polyglycosides (I)

$$R(G)_x \tag{I}$$

where R is a linear saturated alkyl radical having 8 to 22 carbon atoms and $(G)_x$ is a glycoside or oligoglycoside radical having a degree of oligomerization, x, of from 1 to 10 in printing ink cleaners.

The alkyl glycosides (I) are established surface-active substances which can be prepared from sugars and from aliphatic primary alcohols having 8 to 22 carbon atoms with acetalization. Suitable sugar components (glycoses) are preferably glucose, but also fructose, mannose, galactose, telose, gulose, allose, altrose, idose, arabinose, xylose, lyxose, libose, and mixtures thereof.

On account of their ease of availability and good performance properties, preference is given to the acetalization products of glucose with fatty alcohols obtainable, for example, from natural fats and oils by known processes, especially with linear primary saturated and unsaturated fatty alcohols having 8 to 22 carbon atoms.

As far as the glycoside radical $(G)_x$ is concerned, both monoglycosides (x=1), where one sugar radical is linked glycosidically to the fatty alcohol, and oligomeric glycosides, having a degree of oligomerization x=2 to 10, are suitable. In general, mixtures of monoglycosides and oligoglycosides are present.

Preferred and suitable alkyl glycosides (I) are those in which R is an alkyl group having 8 to 22 carbon atoms and $(G)_x$ is a glycoside or oligoglycoside radical having a degree of oligomerization x=1 to 10. With very particular preference, R is an alkyl group having 8 to 14 carbon atoms. The average degree of oligomerization is preferably within the range from 1 to 1.5.

In many cases, the extent of removal of printing inks from solid surfaces can be increased by using the alkyl polyglycosides of the invention in combination with fatty acid esters and/or with one or more surfactants. Said surfactants can be chosen from the classes of the anionic surfactants (except for alkyl polyglycosides (I), which of course are anyway a mandatory constituent of the compounds to be used in accordance with the invention). There are no restrictions whatsoever on the selection of the surfactant; in other words, all relevant anionic, cationic and nonionic surfactants known to the skilled worker can per se be used. The weight ratio of the compounds (I) to the optional constituents mentioned is in the range from 1:20 to 20:1.

In the presence of the alkyl polyglycosides (I) to be used in accordance with the invention it is possible to remove printing inks and/or oil residues, examples being rotary inks for newspapers, letterpress inks, offset inks, publication gravure inks, flexographic inks, laser printing inks and/or packaging gravure inks, from solid surfaces of printing machines, printing plates and the like.

The invention further provides a method of removing printing inks and/or oil residues which form on the surface of printing machines, printing plates and the like and also the associated equipment, which comprises treating said surface with a cleaning composition comprising at least one alkyl polyglycoside (I)

$$R(G)_x \tag{I}$$

where R is a linear saturated alkyl radical having 8 to 22 carbon atoms and $(G)_x$ is a glycoside or oligoglycoside radical having a degree of oligomerization, x, of from 1 to 10.

In one embodiment of this method, the alkyl polyglycosides (I) are used in combination with fatty acid esters (II) of the structure $$R^1-CO_2-R^2 \quad (II)$$

where $R^1$ is a saturated or unsaturated straight-chain or branched alkyl radical having 6 to 23 carbon atoms and the radical $R^2$ is a saturated or unsaturated alkyl radical having 1 to 24 carbon atoms and/or with one or more surfactants.

The examples which follow serve to illustrate the invention and should not be understood as limitative.

EXAMPLES

| Substances used | |
|---|---|
| Glucopon 650 EC: | $C_{8-14}$ alkyl polyglucoside with degree of oligomerization x - 1.5; 50% strength aqueous solution (from Henkel KgaA, Dusseldorf) |
| Glucopon 225 CSUP: | $C_{8-10}$ alkyl polyglucoside with degree of oligomerization x - 1.6; 50% strength aqueous solution (from Henkel KgaA, Dusseldorf) |
| Glucopon 600 EC: | $C_{8-14}$ alkyl polyglucoside with degree of oligomerization x - 1.4; 50% strength aqueous solution (from Henkel KgaA, Dusseldorf) |

Texaprint SRM: rapeseed fatty acid methyl ester (from Henkel KGaA, Dusseldorf)
Texaprint SKEH: coconut fatty acid 2-ethylhexyl ester (from Henkel KGaA, Dusseldorf)
Texaprint SLIB: lauric acid isobutyl ester (from Henkel KGaA, Dusseldorf)
Texaprint AC 3160: anticorrosion agent (from Henkel KGaA, Dusseldorf)
Disponil TL 55: nonionic surfactant (from Henkel KGaA, Dusseldorf)
Dehydol LS 57: nonionic surfactant (from Henkel KGaA, Dusseldorf)

The amounts in the following examples are parts by weight.

Example 1

50 parts of TEXAPRINT SRM
40 parts of water
3 parts of TEXAPRINT AC 3160
2 parts of Disponil TL 55
5 parts of Glucopon 650 EC

Example 2

50 parts of TEXAPRINT SKEH
40 parts of water
3 parts of TEXAPRINT AC 3160
5 parts of Glucopon 215 CSUP
2 parts of Dehydol LS 7

Example 3

50 parts of TEXAPRINT SLIB
42 parts of water
3 parts of TEXAPRINT AC 3160
5 parts of Glucopon 600 EC

Application Example

Several thousand sheets of paper were printed on a Heidelberg offset printing machine. The rollers were then washed with the cleaner formulations of Examples 1 to 3. The printing ink was removable rapidly and without problems, and the cleaner emulsion could be rubbed off from the rolls without residue.

What is claimed is:

1. A process for removing printing inks and/or oil residues located on a surface of a printing apparatus comprising:

(a) contacting the printing inks and/or oil residues with a cleaning composition containing an alkyl polyglycoside corresponding to formula (I):

$$R(G)_x \quad (I)$$

wherein R is a linear saturated alkyl radical having from 8 to 22 carbon atoms, and $(G)_x$ is a glycoside or oligoglycoside radical having a degree of oligomerization, x, of from 1 to 10 to form a printing ink and/or oil residue emulsion; and (b) removing the printing ink and/or oil residue emulsion from the surface of the printing apparatus.

2. The process of claim 1 wherein R is an alkyl group having from 8 to 14 carbon atoms.

3. The process of claim 1 wherein G is a glucoside radical.

4. The process of claim 1 wherein the cleaning composition further comprises a fatty acid ester corresponding to formula (II):

$$R^1-CO_2-R^2 \quad (II)$$

wherein $R^1$ is a saturated or unsaturated, straight-chain or branched alkyl radical having from 6 to 23 carbon atoms, and $R^2$ is a saturated or unsaturated, alkyl radical having from 1 to 24 carbon atoms.

5. The process of claim 4 wherein the alkyl polyglycoside and fatty acid ester are present in the cleaning composition in a ratio by weight of from 1:20 to 20:1.

* * * * *